United States Patent
Murphy et al.

(10) Patent No.: US 7,983,995 B2
(45) Date of Patent: Jul. 19, 2011

(54) SYSTEM AND METHOD FOR DISPENSING, SORTING AND DELIVERING PRESCRIPTION AND NON-PRESCRIPTION MEDICATIONS THROUGH THE POST OFFICE

(75) Inventors: Michael J. Murphy, Salem, NH (US); Pamela A. Hoodes, Acton, MA (US)

(73) Assignee: The Escher Group, Ltd., Cambridge, MA (US)

( * ) Notice: Subject to any disclaimer, the term of this patent is extended or adjusted under 35 U.S.C. 154(b) by 200 days.

(21) Appl. No.: 11/274,966

(22) Filed: Nov. 15, 2005

(65) Prior Publication Data

US 2006/0122729 A1 Jun. 8, 2006

Related U.S. Application Data

(60) Provisional application No. 60/628,150, filed on Nov. 15, 2004.

(51) Int. Cl.
*G06Q 30/00* (2006.01)
*G06F 7/00* (2006.01)

(52) U.S. Cl. ............ 705/332; 705/330; 705/2; 700/216; 700/220

(58) Field of Classification Search ............... 705/1, 332, 705/330, 2; 700/216, 220
See application file for complete search history.

(56) References Cited

U.S. PATENT DOCUMENTS

| | | | | |
|---|---|---|---|---|
| 3,387,699 A * | 6/1968 | Heller | | 206/531 |
| 5,492,616 A * | 2/1996 | Cook et al. | | 206/591 |
| 5,917,925 A * | 6/1999 | Moore | | 382/101 |
| 6,024,278 A * | 2/2000 | Martin | | 229/92.8 |
| 6,382,412 B1 * | 5/2002 | Wood | | 206/232 |
| 6,762,384 B1 * | 7/2004 | Kechel | | 209/584 |
| 6,769,228 B1 * | 8/2004 | Mahar | | 53/411 |
| 7,028,723 B1 * | 4/2006 | Alouani et al. | | 141/83 |
| 2003/0062293 A1 * | 4/2003 | Graushar et al. | | 209/1 |
| 2004/0011806 A1 * | 1/2004 | Luciano et al. | | 221/266 |
| 2004/0019794 A1 * | 1/2004 | Moradi et al. | | 713/185 |

(Continued)

FOREIGN PATENT DOCUMENTS

EP 1388336 2/2004

OTHER PUBLICATIONS

"Novartis Saves $122,000 on Sample Mailing", Direct v.15, n.5, Apr. 1, 2003.*

*Primary Examiner* — John W Hayes
*Assistant Examiner* — Kevin Flynn
(74) *Attorney, Agent, or Firm* — Cesari and McKenna, LLP; Patricia A. Sheehan

(57) ABSTRACT

A pharmacy post office receives prescriptions and produces through an automated pill dispensing and packaging system machine-sortable pharmacy letters that are sortable by automated mail sorting machines into postal delivery routes and delivered as first class or priority mail pieces by the postal delivery persons along their customary routes. A track and trace system may provide a delivery schedule to the patient and/or prescribing doctor based on the time of day the pharmacy letter is provided to the automated mail sorting machines. When a pharmacy letter is delivered by the postal delivery person, he or she scans the tracking code and transmits information back to the track and trace system, which then updates its delivery schedule to show the completed delivery.

21 Claims, 15 Drawing Sheets

U.S. PATENT DOCUMENTS

| | | |
|---|---|---|
| 2004/0064326 A1* | 4/2004 | Vaghi ................................ 705/1 |
| 2004/0123567 A1 | 7/2004 | McErlean et al. |
| 2004/0158350 A1 | 8/2004 | Ostergaard et al. |
| 2005/0071291 A1* | 3/2005 | Mayer et al. ................. 705/401 |
| 2005/0209879 A1* | 9/2005 | Chalmers .......................... 705/2 |
| 2006/0042988 A1* | 3/2006 | Hjalmarsson ................. 206/539 |
| 2006/0074521 A1* | 4/2006 | Rice et al. ..................... 700/216 |

* cited by examiner

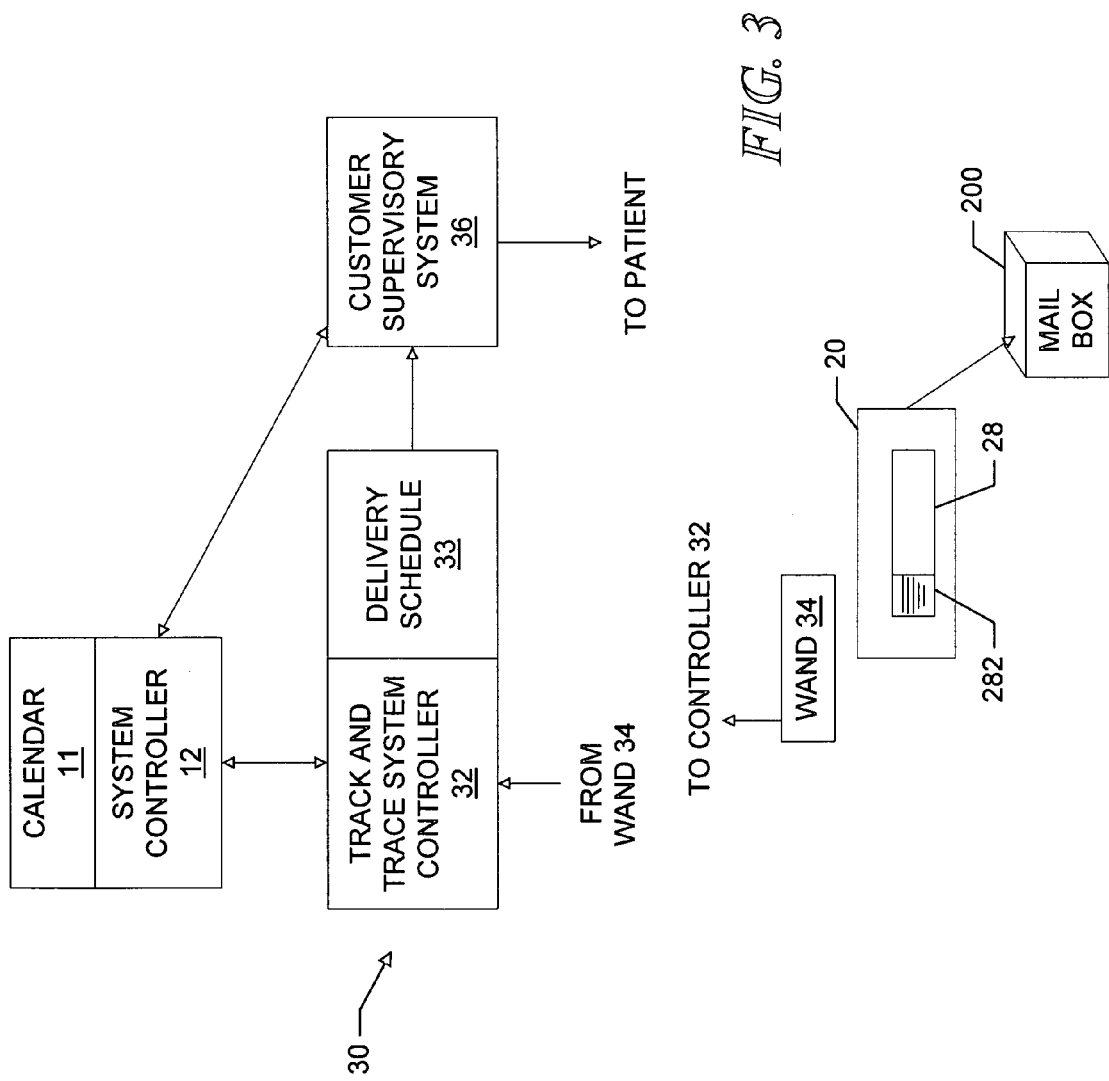

SYSTEM AND METHOD FOR DISPENSING, SORTING AND DELIVERING PRESCRIPTION AND NON-PRESCRIPTION MEDICATIONS THROUGH THE POST OFFICE

CROSS-REFERENCE TO RELATED APPLICATION

The present application claims the benefit of U.S. Provisional Patent Application Ser. No. 60/628,150, which was filed on Nov. 15, 2004, by Michael J. Murphy for a SYSTEM FOR DISPENSING, SORTING AND DELIVERING PRESCRIPTION AND NON-PRESCRIPTION MEDICATIONS THROUGH THE POST OFFICE and is hereby incorporated by reference.

FIELD OF THE INVENTION

The invention relates generally to automated systems and methods for filling prescriptions and, more particularly, to automated systems and methods for packaging, sorting and delivering the prescription medications.

BACKGROUND INFORMATION

Nursing homes and hospitals have begun using pre-packaged prescription medications in an effort to alleviate errors in the dispensing of the medication. A medication in pill form may be packaged in strips or sheets, from which a desired dosage can be selectively detached. The nurse who provides the medication to the patient thus removes the appropriate number of pills on a per patient per day basis from the strip or sheet and hand delivers the pills to the patient. The pre-packaged dispensing eliminates the step of counting the pills out of bottles or containers, which tend to look alike and can be easily confused. Further, the pre-packaged dispensing reduces dosing errors by ensuring that the pills provided have the correct strength.

The pre-packaged dispensing of the medications also provides more accountability and less chance for inadvertent or intentional diversion of the medications. The multiple-pill strips or sheets can, for example, be individually identified and inventoried. Further, pills can not be readily stolen or misdirected in small amounts that might otherwise go undetected.

For the same reasons, namely, to reduce errors in the selection of medications to fill prescriptions and to reduce loss and/or theft of medication, commercial pharmacies have begun using automated pill dispensers. The pills are delivered to the machine by the manufacturers in machine-accessible canisters. For each prescription, the pill dispensing machine selects the appropriate canister, counts out the pills and then dispenses the pills to the pharmacist. The pills may, for example, be dispensed into a conventional pill bottle or other receptacle. The pharmacist then prints out a label that includes prescription-related information, such as the prescription number, the medication name, instructions for taking the medication and so forth and attaches the label to the bottle. The medication is then available for pick-up by the prescription holder. The pharmacist does not otherwise have access to the pills and thus cannot inadvertently select the wrong pills, miscount the pills or intentionally divert pills.

Automated pill dispensers solve some but not all of the problems associated with the filling of prescriptions in commercial pharmacies. One continuing problem is persuading the patients to bring the prescriptions to the pharmacy for filling in the first place. Patients may be reluctant to fill prescriptions or to take certain medications for various reasons, such as cost, embarrassment, and so forth. Elderly patients may have difficulty in actually getting to the pharmacy because of disabilities and/or difficulty in arranging transportation. Also, patients may have difficulty in determining or managing when to re-fill a given prescription. The problems are compounded if a patient is taking multiple medications that may have different re-fill dates, and so forth.

Certain prescription medications may be ordered through mail order companies, which use third party delivery services to provide home delivery of the medications. The doctors or the patients contact a given mail order company and initiate the prescription filling process. The mail order company verifies the prescription, as appropriate, dispenses the medication, packages the medication for shipping and provides the packages to a local office of the third party delivery service. The delivery service then transports the packages by air, truck or rail to various delivery offices that are local to the patients and the local offices then deliver the packages to the patients' homes.

The mail ordering of the medication solves certain problems associated with, for example, the inability of patients to travel to the pharmacy to pick up the medications. However, the mail ordering of the medications increases the cost of obtaining the medication by adding thereto the third party delivery expenses. Further, the mail ordering adds complexity to the process of providing the medication by adding steps in which the medication is handled by people at the mail order company and people at the various offices of the delivery service. Each handling step increases the chances that medication may be lost, or inadvertently or intentionally diverted.

Further, the mail ordering of the medication from the mail ordering company eliminates any personal interaction between the patient and a local pharmacist. Thus, the patient may not be adequately advised about how the medication should be taken, side effects to watch for, and so forth. Accordingly, the patient may experience problems associated with the improper handling of the medication, or a failure to react to particular side effects of the medication.

Other problems are associated with having the relatively large quantities of medication, i.e., months worth of pills, at a user's discretion. If the pills command a high street price, for example, the user may sell some or all of the pills and thus chance the worsening of the malady to which the pills are directed. Further, the medication may, in the quantity provided be toxic. Thus, children or forgetful adults may end up poisoning themselves. Accordingly, what is needed is a system for delivering medication that is efficient, accurate and priced per delivery to allow for frequent re-filling deliveries.

SUMMARY OF THE INVENTION

The invention is a pharmacy post office that receives prescriptions and through an automated pill dispensing system and packaging system produces pharmacy letters that are sorted and delivered as first class or priority mail pieces. The system packages the pills in carriers that are sufficiently rigid to protect the pills yet are sized to fit into sorting machines that sort the first class or priority mail pieces. The pharmacy letters include patient address information such that the pharmacy letters are then fed to the mail sorting machines and sorted along with the first class or priority mail pieces for same or next day delivery by the postal delivery persons along their customary routes. The cost of packaging and delivery of the pharmacy letters is such that prescriptions can be filled in installments, to avoid, for example, delivery of toxic amounts of medication. The pharmacy operations may also be combined with GIS information to produce pharmacy letters for all residents in a designated geographic area in response to an outbreak such as SARS or bird flu.

The system includes a robotic subsystem that dispenses pills from pill canisters provided by the drug companies and provides the pills to an automated packaging system. The packaging system feeds the pills into compartments of a carrier base, or blister pack, and prints on a carrier lid drug identification information, patient identification information and tracking information, such as a machine readable code. The packaging system then folds over the lid and seals the carrier, leaving patient address information available for reading by mail sorting machines. Alternatively, mailing labels are applied to the carrier or the carrier is inserted into an addressed carrier mailing envelope. The assembled pharmacy letter is then supplied to the mail sorting machines and included in the first class or priority delivery operations of the post office.

A track and trace system may be included to provide a delivery schedule to the patient and/or prescribing doctor. The track and trace system is informed when the packaging system provides a pharmacy letter to the mail sorting machines. The track and trace system receives the corresponding tracking identifier code and the date and time of delivery to the sorting machines. Based on the time, the track and trace system determines if the pharmacy letter will be included in the same day postal delivery operations or in the next day operations, and the track and trace system adds the pharmacy letter to its delivery schedule. The patients can then view relevant portions of the delivery schedule on-line, to determine when to expect their medications.

The postal delivery persons scan the pharmacy letters when they drop off the letters at the patients' drop sites, and transmit the scanned information to the track and trace system. The track and trace system then updates its delivery schedule to show the completed delivery. As appropriate, the track and trace system notifies a customer supervision system of the delivery and the customer supervision system contacts the patient to discuss how the pills are to be taken, and so forth.

The track and trace system may be expanded to track and trace the delivery of the pills from the manufacturer by including tracking codes on the pill containers and reporting the time and date the containers leave the manufacturer's facility. The track and trace system then monitors when the containers arrive and the condition of the containers on arrival at the pharmacy post office, and makes the information available to the manufacturer. The manufacturer may also be notified when pills are dispensed from the respective containers, such that the manufacturer can keep track of when to supply additional containers to the pharmacy post office in order to replenish the inventory.

The inventive system thus automates the filling and delivering of prescription medication and does so in an efficient manner that is secure, reliable and cost effective.

BRIEF DESCRIPTION OF THE DRAWINGS

The invention description below refers to the accompanying drawings, of which:

FIG. 3 is a functional block diagram of a track and trace system and a customer supervisory system that are constructed in accordance with the invention and operate with the system of FIG. 1;

DETAILED DESCRIPTION OF AN ILLUSTRATIVE EMBODIMENT

Figure 1:
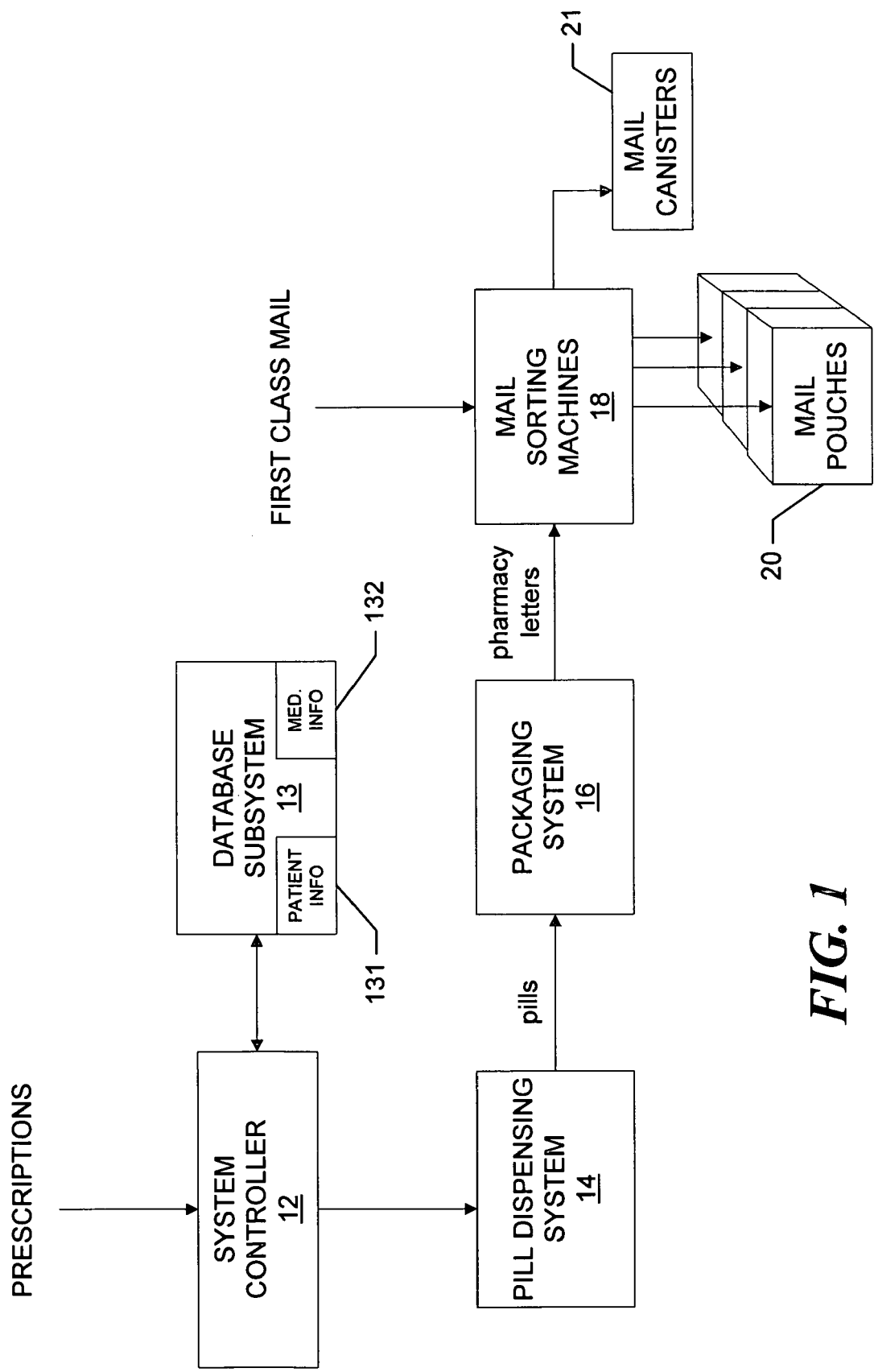
FIG. 1 is a functional block diagram of a system that is constructed in accordance with the invention.

Referring now to FIG. 1, an automated prescription medication delivery system, or pharmacy-post office, 10 includes a system controller 12 that receives prescriptions electronically by secure e-mail or by key in, checks for drug interactions and adverse medical conditions using a database subsystem 13 that contains both patient and medication information, and assigns identifiers to the prescriptions. The controller then enters the prescriptions in the database subsystem 13, and provides prescription-related information and associated instructions to an automated pill dispensing system 14. The pill dispensing system, which operates in a known manner, dispenses the medications, i.e., pills, gelcaps and so forth, all of which are referred to hereinafter collectively as "pills," in accordance with the prescriptions.

The pill dispensing system provides the dispensed pills to a packaging system 16 that also receives the prescription-related information, which includes the assigned identifiers, and the patient contact information from the system controller. The pill packaging system organizes the pills and packages them in an appropriately rigid carrier 20 (FIGS. 2A-E) that meets the size constraints of first class, or priority, letter mail. The packaging system also prints, directly on the carrier and/or on one or more labels 28 that are later affixed to the carrier or to a carrier mailing enclosure 27, a mailing address, is medication specific information and a machine readable code, such as a bar code, that identifies the package and/or associates the contents of the package with one or more prescriptions. Alternatively or in addition, the system may include on the carrier an RFID tag (not shown) that provides the code. The assembled and addressed carrier is hereinafter referred to as a "pharmacy letter." As discussed in more detail with reference to FIG. 3 below, the machine readable code is preferably used to provide information to a track and trace system 30. As further discussed below, the operations of the track and trace system may be expanded to include the tracking and tracing of medications from the manufacturer to the pharmacy-post office.

The packaging system 16 provides the pharmacy letters to mail sorting machines 18. The mail sorting machines operate in a known manner to sort first class, or priority, mail pieces by postal routes based on the respective mailing addresses. By packaging the prescription medications in the appropriately-sized carriers, as opposed to traditional pill bottles and/or containers, the system 10 takes advantage of the sorting capabilities of the machines 18, such that the sorting machines sort the pharmacy letters along with conventional mailpieces for same or next day delivery by the postal delivery persons.

The sorting machines 18 provide the sorted pharmacy letters along with conventional sorted first class, or priority, mail pieces to the appropriate mail delivery containers, such as, carrier mail pouches 20 or mail canisters 21, which are used for delivery of mail to local post offices that then further sort the mail into the carrier pouches. The pharmacy letters are thus included in the daily postal service first class, or priority, mail delivery operations.

Figure 4:
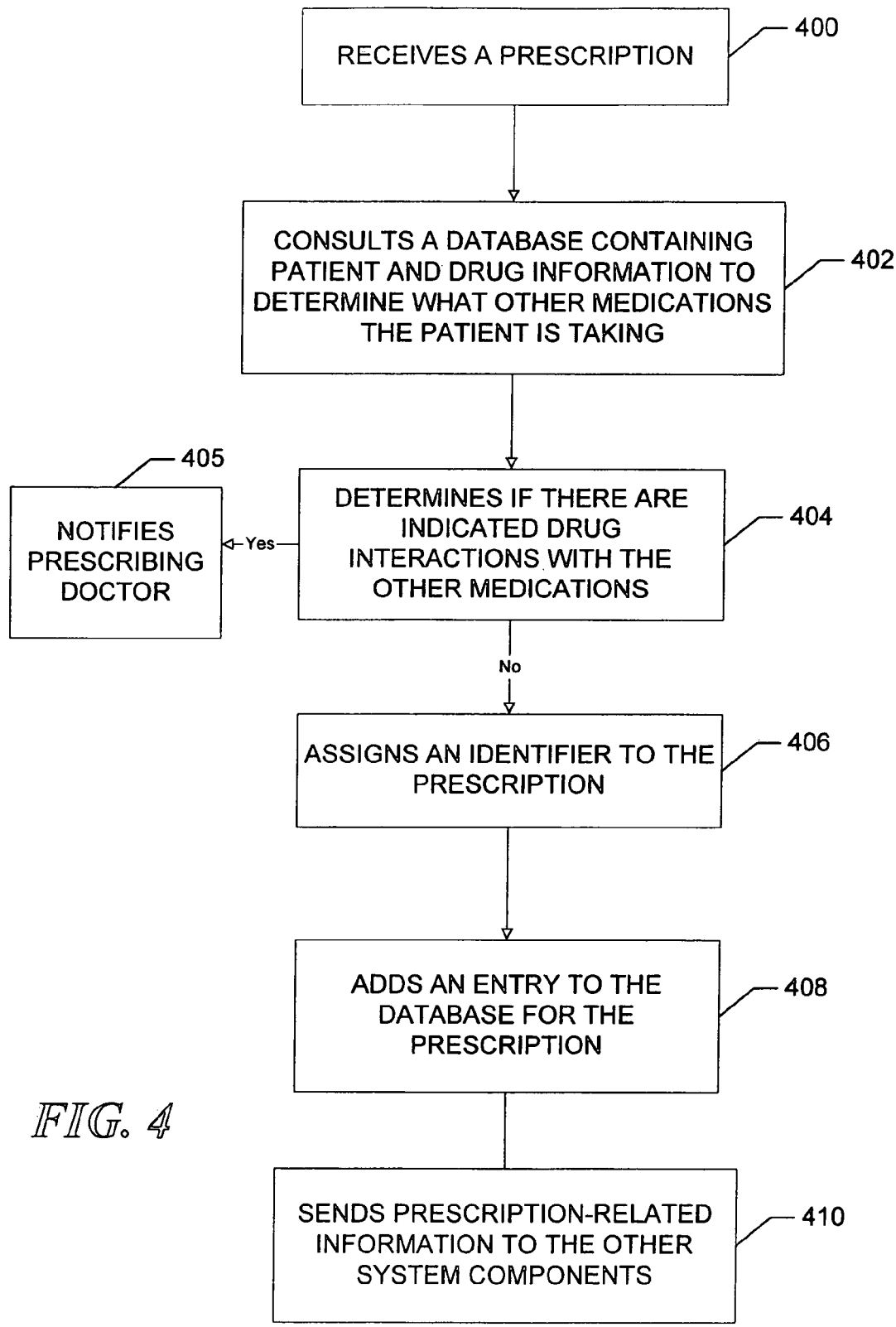
FIGS. 4-8 are flow charts of the operations of the systems of FIGS. 1 and 3.
Figure 5A:
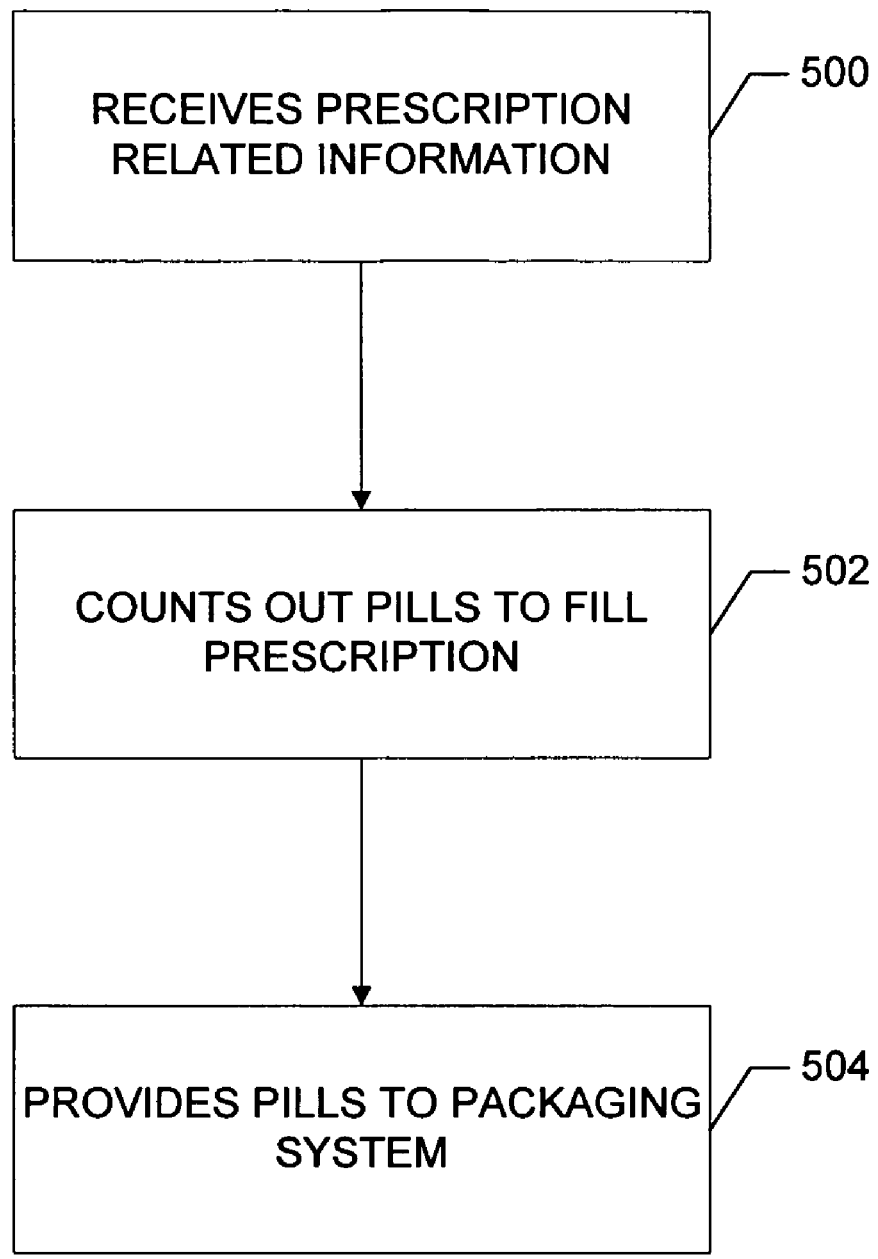
Figure 5B:
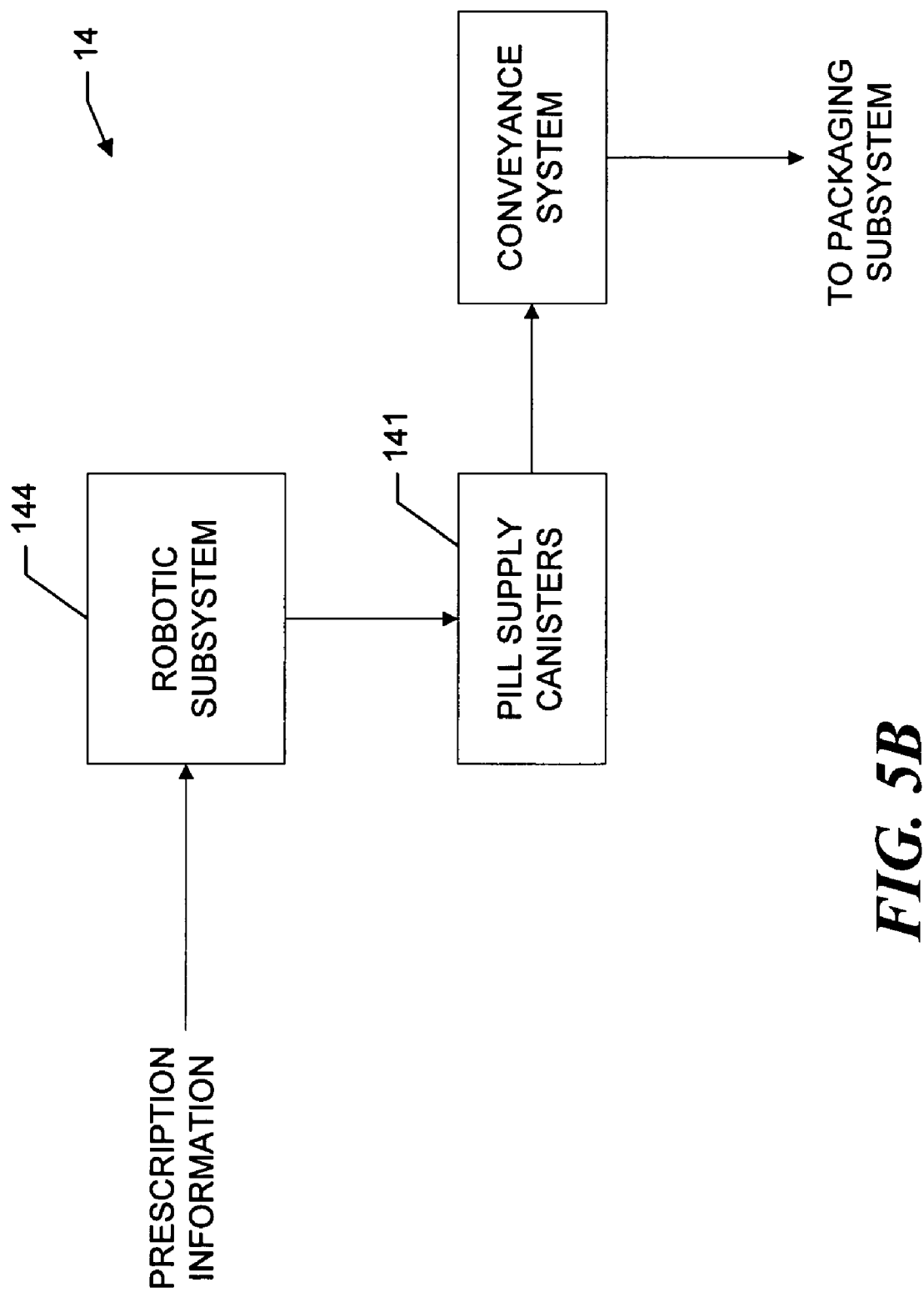
Figure 6A:
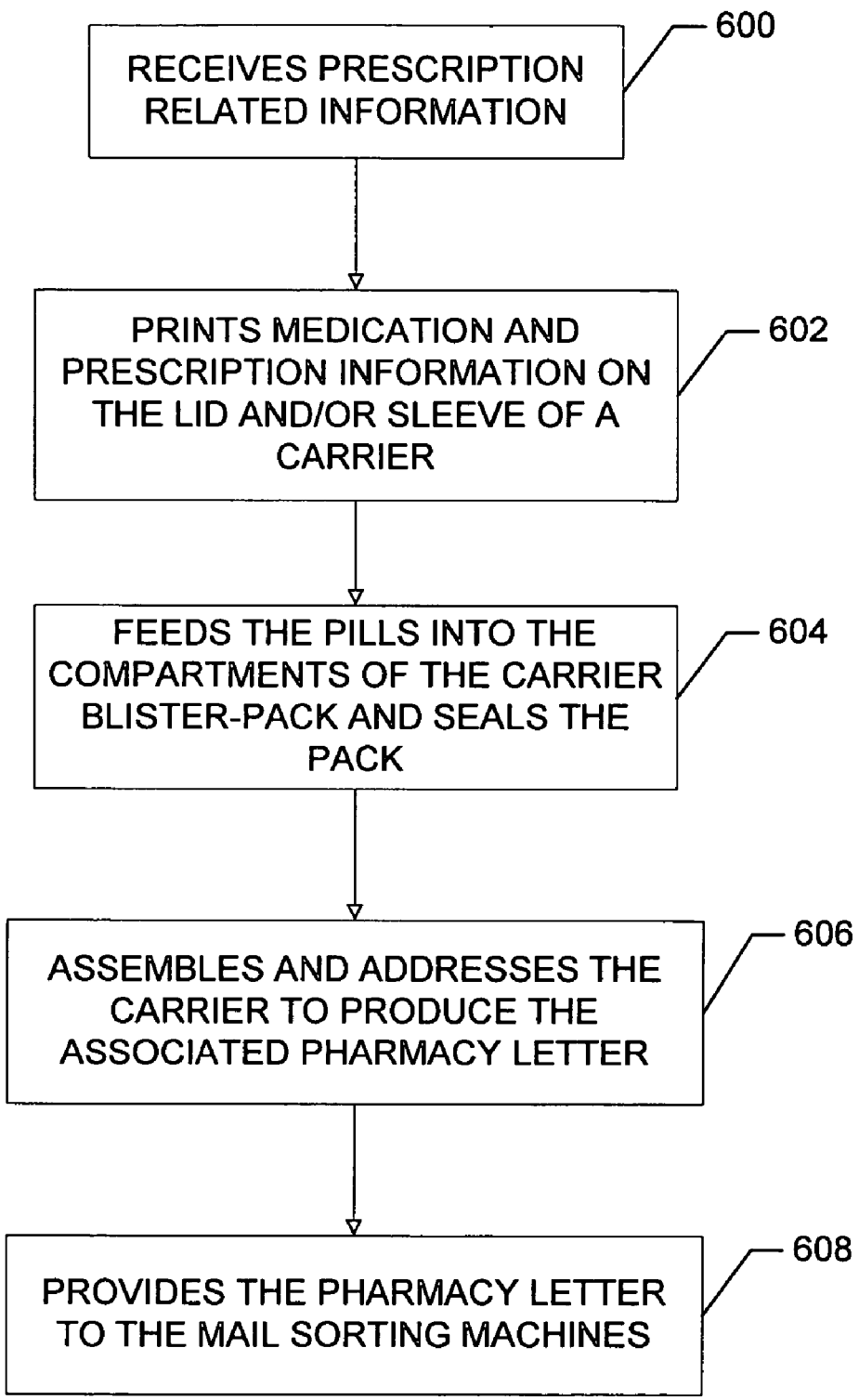
Figure 6B:
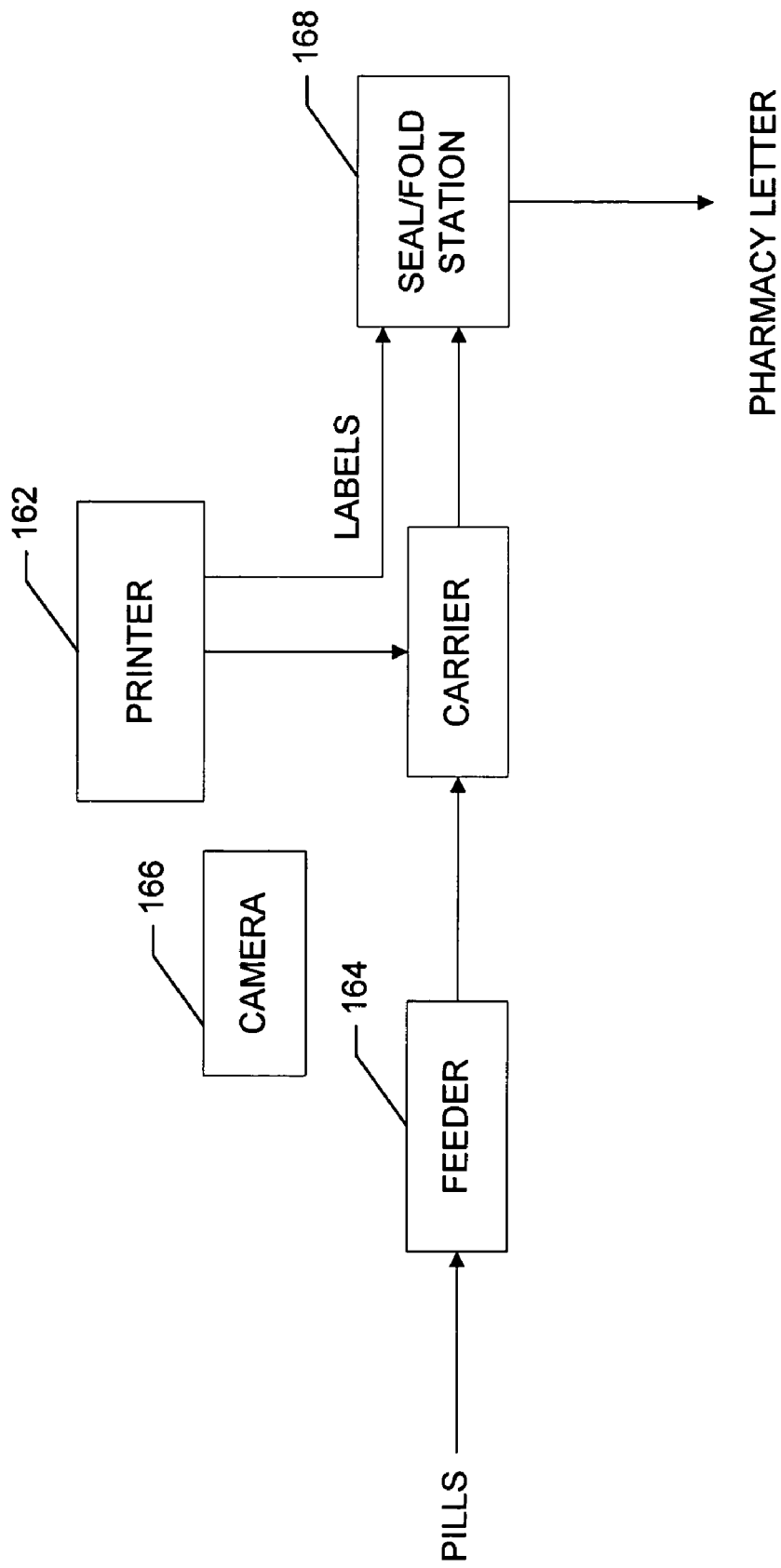

The postal delivery personnel hand deliver the machine-sorted pharmacy letters to mail drop points 200 (FIG. 4), such as, mail boxes, letter slots and so forth that are on their customary postal routes. Thus, prescriptions received by the system 10 before the morning mail sorting deadline can be filled, sorted and hand-delivered along postal routes to the patients in the same day, for a delivery cost of pennies. Further, there is little or no human intervention in the process of filling the prescription and delivering the medication, except the hand delivery of the sealed pharmacy letters to the mail drop points, and thus, the pills can be tracked and traced from the manufacturer's container to the respective patients.

Referring now also to FIGS. 2A-E, the packaging system 16 packages the medication in carriers 20 that are within the size constraints of the mail sorting machines 18 and are sufficiently rigid to prevent the crushing of the pills by the sorting machines. Known mail sorting machines are currently capable of sorting pieces that are up to 7 millimeters thick. Accordingly, in the embodiment the packaging system packages the pills in carriers that are at most 7 millimeters thick. The carrier 20 preferably includes a base, or blister pack, 21 with individual compartments 22 for the pills 200 and a lid 24 that is attached to and folds over the top surface 23 of the blister pack. After the lid is folded over the blister pack, the two sections of the carrier may be sealed together around one or more edges.

The carrier 20 further includes a sleeve 26 that slides over the blister pack 21, or alternatively, into which the blister pack is inserted. The sleeve may include one or more ends (not shown) that seal, to produce a carton that encloses the blister pack. Alternatively, or in addition, the assembled carrier may be wrapped and sealed by, for example, shrink wrapping, to provide further tamper resistance. For privacy reasons, the wrapping may obscure certain or all of the medication prescription specific information and/or the assembled carrier may slide into a carrier mailing envelope 27.

Figure 2A:
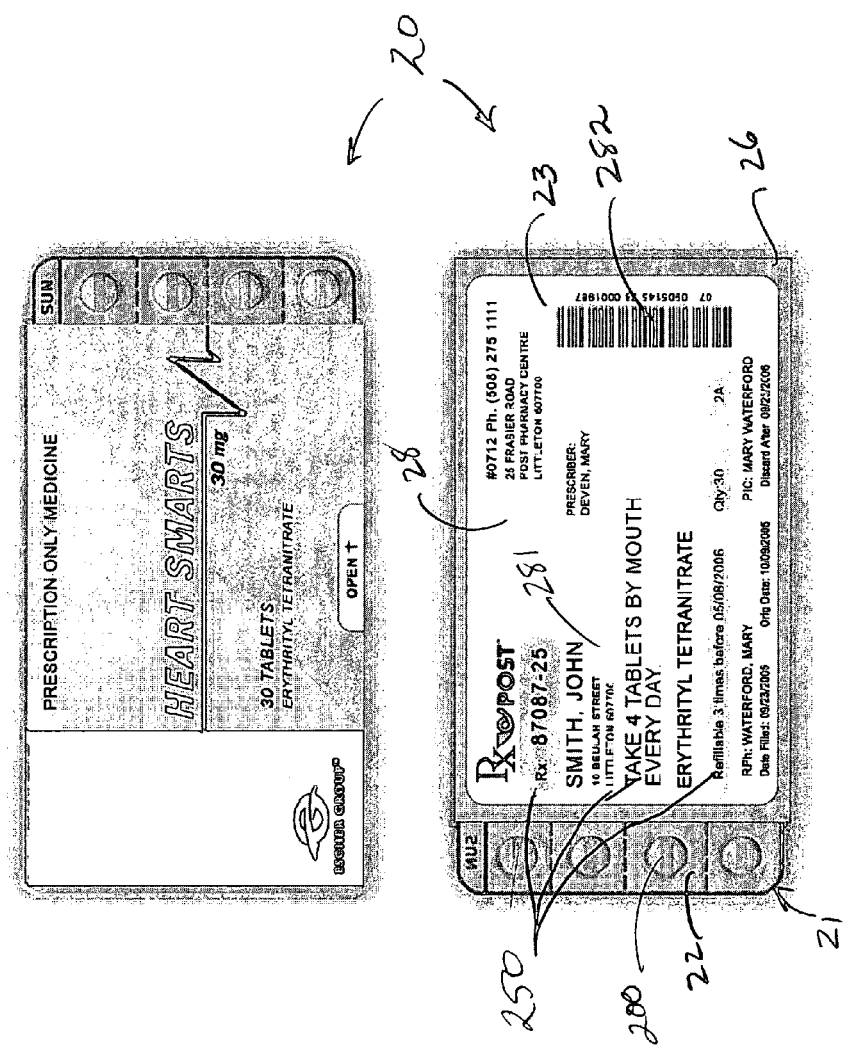
FIGS. 2A-E illustrate carriers use for in the system of FIG. 1.
Figure 2B:
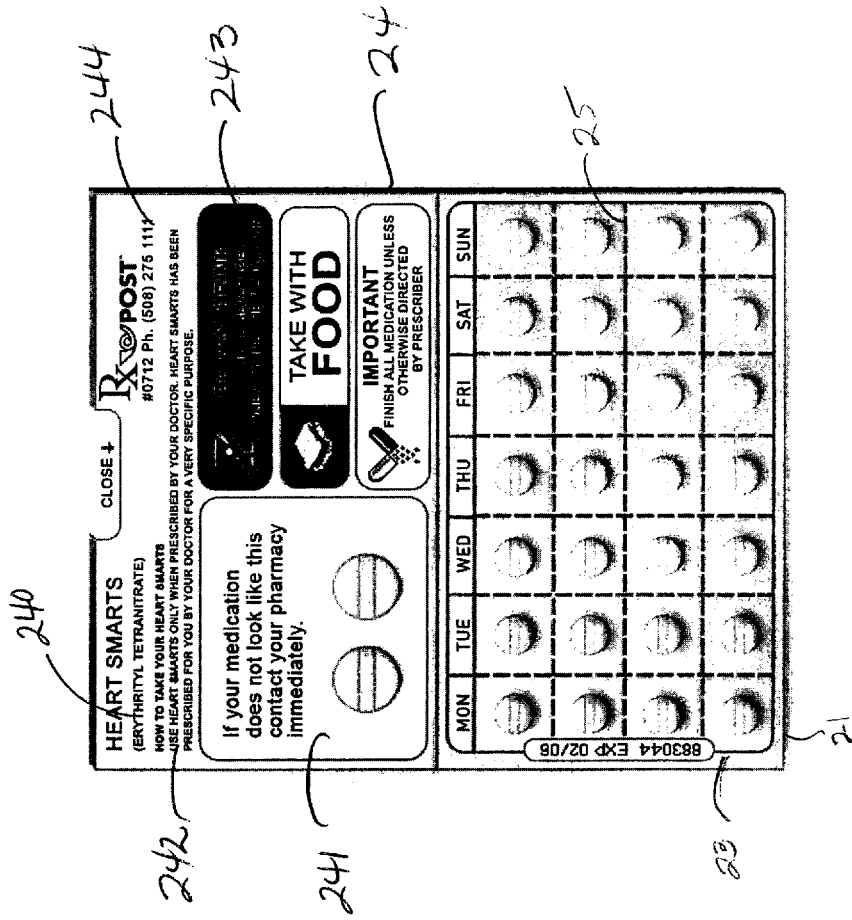
Figure 2C:
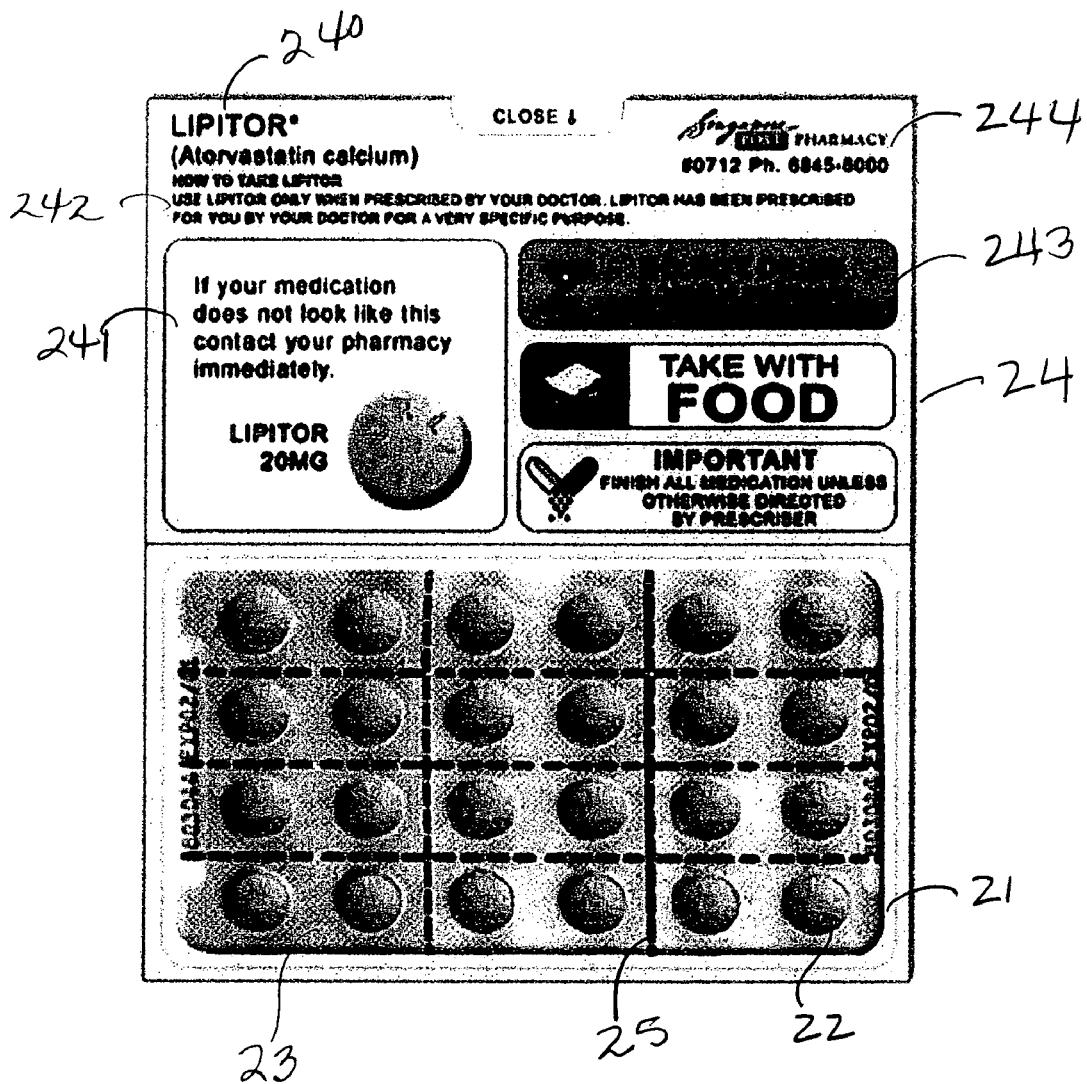
Figure 2D:
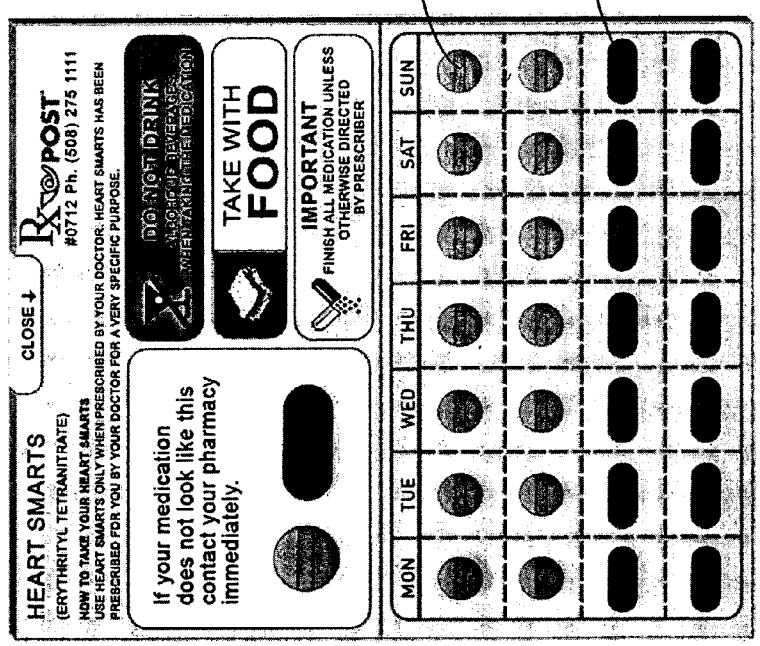
Figure 2E:
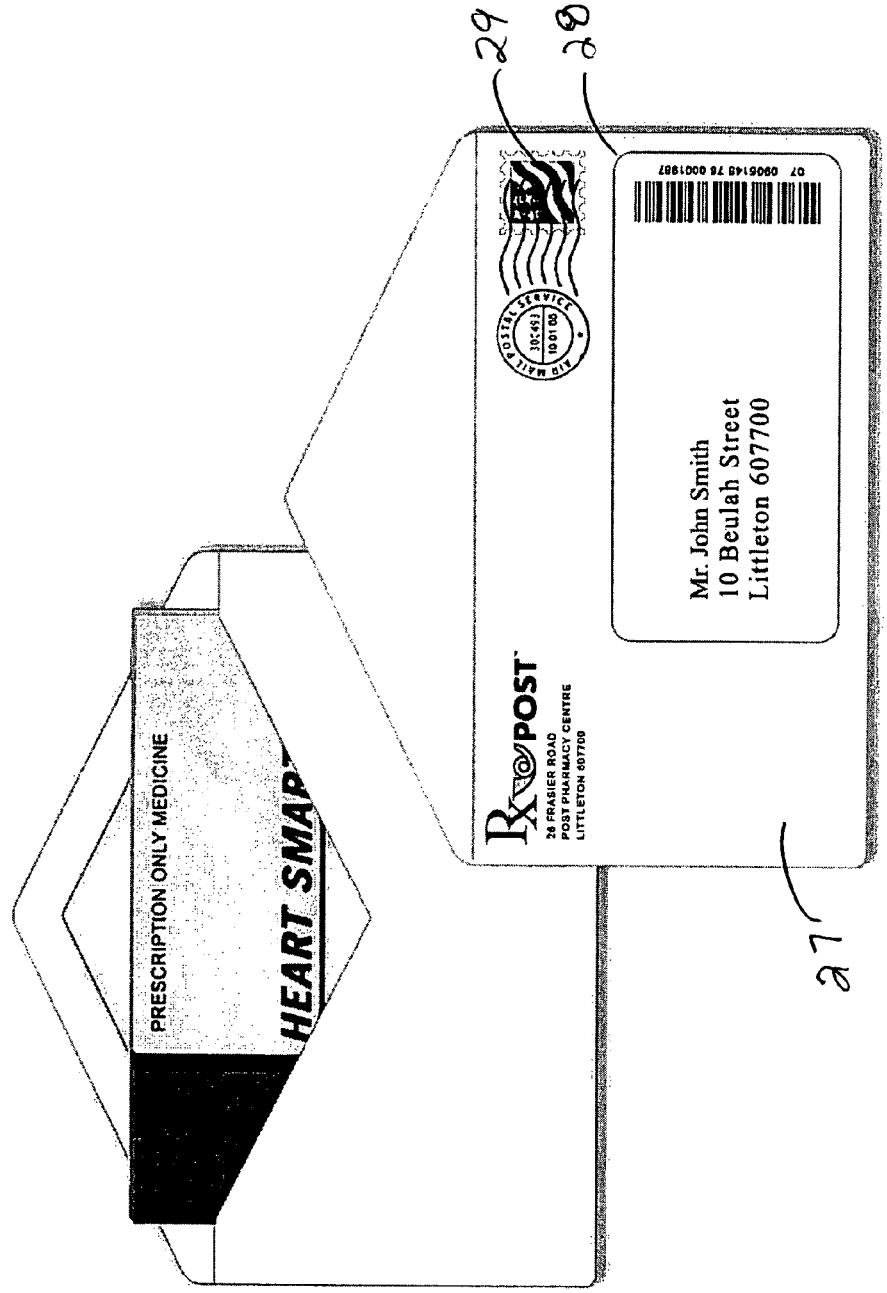

The packaging system may package one prescription (FIG. 2A) or several prescriptions (FIG. 2D) in a given carrier 20. When a patient is prescribed more than one medication or when a dose requires more than one pill 200, the packaging system 20 essentially groups the compartments (FIG. 2C), to denote the different medications, and/or the medications that are to be taken together, taken in the same day, and so forth. As shown in FIG. 2C, two-pill dosage groupings are denoted by lines 25, which may be printed on the top surface 23 of the blister pack 21 or embedded in the surface as, for example, perforation lines. The packaging may be similarly organized for days of the week, weeks of the month, and so forth, as depicted in FIG. 2B. As shown in FIG. 2D, pills 200 and 201 of varying shapes may be included in the same carrier.

Before loading the medication into the blister pack 21, the packaging system 16 prints medication-specific information on the lid 24. As shown in the drawing, the lid has printed thereon the name of the medication 240, a picture of what the prescribed pill looks like 241, general instructions for taking the medication 242, and various labels 243 that remind or warn the user about conditions associated with the use of the medications, such as taking with food, without alcohol, and so forth. In addition, pharmacy-specific information 244 may also be included on the lid. Further, prescription-specific information 250, such as the assigned identifier, the quantity of pills, specific instructions for taking the medication and so forth, may be included on the lid and/or on a mailing label 28 that is also printed for the carrier by the packaging system.

The packaging system 16 may print the mailing label 28 directly on the sleeve 26 or on a carrier mailing envelope 27 that receives the assembled carrier. Alternatively, the packaging system may print a separate label and it may then affix the label to the sleeve or the envelope either before or after the carrier is assembled.

The mailing label 28 includes the delivery address 281 and a machine readable code 282, shown in the drawing as a bar code. The code 282 identifies the pharmacy letter and may also identify the medications that are included in the pharmacy letter and/or the associated prescription or prescriptions. The code 282 is used to track and trace the pharmacy letter from its assembly by the packaging system to its hand delivery at the designated mail drop point, as discussed in more detail with reference to FIG. 3 below. The prescription-specific information 250 may also included on the mailing label. Alternatively, the prescription-specific information may instead be printed on a dedicated label 29 that is attached to the carrier before the carrier is inserted into the carrier envelope.

The packaging system 16 may also include in the carrier a printed sheet (not shown) that provides medication specific information relating to drug interactions, side effects, and so forth, as may be required by government regulations. When an insert is required, the controller 12 instructs the packaging system to print an associated file or instead sends the file to the packaging system for printing. The packaging system then either inserts the printed sheet into the assembled carrier or wraps the sheet around the blister pack 21 before the sleeve 26 slides over the pack, or alternatively before the pack is inserted into the sleeve 26.

The carrier may include an RFID tag (not shown), which may be used to provide the machine readable code instead of or in addition to the printed code 282. Further, postage 29 is applied to the assembled carrier or the envelope 27 either separately or as part of the mailing label 28.

Referring now also to FIG. 3, the track and trace system 30 collects and manages information relating to the scheduled and the actual delivery of the pharmacy letters. As discussed below, the track and trace system may further collect and manage information relating to delivery of the pills in quantity from the manufacturer to the pharmacy post office.

When a prescription enters the system, the system controller 12 provides to a track and trace system controller 32 the prescription-related information, which includes the assigned identifier and also the date and time that prescription was received. The track and trace system then adds the information to a delivery schedule maintained by the track and trace system, and lists the delivery of the associated pharmacy letter for same day delivery if the prescription arrives before a mail sorting cut-off time or otherwise for next-day delivery. If two or more prescriptions are to be combined in the same pharmacy letter, the system controller provides appropriate instructions and prescription related information to control the pill dispensing and packaging operations and inform the track and trace operations of the combination.

When the pharmacy letter is assembled by the packaging system 16, the packaging system 16 notifies the system controller 12 and the track and trace system 30. The track and trace system then updates the delivery schedule, as appropriate, based on the pharmacy letter meeting or falling behind the mail sorting deadline for same day delivery.

When the pharmacy letter is hand delivered to the mail drop point 200, the postal delivery person scans the code 282 on the mailing label 28 or an included RFID tag, (not shown) using a wand 34. The wand 34 transmits the coded information to the track and trace system 30, to instantly inform the system of the delivery. The track and trace system updates the delivery schedule and sends a message to the customer supervisory system 36, to inform the supervisory system of the delivery of the identified pharmacy letter. The customer supervisory system, in turn, requests patient and medication information from the controller 12, and directs a staff nurse practitioner or pharmacist to contact the patient and confirm that the correct medication was delivered and/or discuss any concerns or questions that the patient may have with respect to the medication.

If the medication is new to the patient, the customer supervisory system 36 directs the staff nurse or pharmacist to discuss how the medication is to be taken with the patient. At the same time, the caller may reconfirm that the patient knows the number to call for answers to questions concerning the medication. Further, the caller may also check the accuracy of the delivery environment information that is retained by the system relating to, for example, the presence or absence of small children or pets at the address. The customer supervisory system, by calling the patient at the time the pharmacy letter is delivered, provides the same sort of personal attention to the patient that a pharmacist provides when a prescription is picked up in person at the pharmacy.

Before a first delivery is made to a new patient and/or mail delivery point, the customer supervision system 36 contacts the patient to discuss the delivery environment. When the controller 12 receives a prescription that is directed, for example, to a patient that is not included in the database 13, the controller notifies the customer supervision system. The customer supervision system then calls the patient, to ask the patient questions concerning the delivery environment. As necessary, the customer supervisory system prepares special delivery instructions for the postal delivery person that is assigned to the postal route that includes the patient. The delivery instructions may, for example, require delivery to a mail box as opposed to delivery through a mail slot in the door, or delivery to a locked mail box, and so forth.

The system controller 12 may further oversee just-in-time delivery operations that ensures that refills of the medications are packaged into pharmacy letters and delivered to the patients on the appropriate days, without requiring the patient and/or the doctor to initiate the refill process. The system controller 12 receives from the track and trace system controller 32 delivery confirmation information for the respective prescriptions. On receipt of the delivery confirmation information, the system controller enters the database subsystem 13 to determine if a given prescription can be refilled, based on how many pills have been delivered by the system to the patient and/or the expiration date of the prescription. If there are refills remaining, the system controller determines, from the associated dosage and delivery information, the date for a next delivery of the pills. Further, the controller determines if other medication should be delivered on the same date. The controller then provides the date and prescription identifier(s) to a calendar subsystem 11.

The calendar subsystem 11 sets the date in its calendar and thereafter, on the indicated date, the notifies the system controller 12. The controller then starts the process of preparing the appropriate pharmacy letter by sending the appropriate information to the pill dispenser system 14 and the packaging system 16. In response, the two systems operate to prepare the pharmacy letter and provide the pharmacy letter to the mail sorting machines 18 in the manner described above. The medication is then delivered to the appropriate mail drop points as also discussed above. The just in time operations are discussed in more detail below with reference to FIG. 9.

When a pharmacy letter containing re-filled prescription medication is delivered, the customer supervisory system 36 may direct that the call to the patient include questions relating to how the patient is taking the medication, and so forth, to check that the patient is following the doctor's orders.

When the system controller 12 determines that a prescription has run out because of either the expiration date or the total number of pills dispensed, the system controller may notify the prescribing doctor and request permission for additional re-fills. Alternatively, the service may notify the patient that the pharmacy letter contains the last re-fill by, for example, instructing the packaging system to print the information on the lid 24 of the carrier 20 or on an insert (not shown). Alternatively, the system controller may notify the customer supervisory system 36, which may then contact the patient directly by telephone, email or regular mail.

For medications that are toxic in relatively large doses, either for adults or children, the system controller may use the just-in-time delivery operations to fill prescriptions in multiple installments, with each installment including a quantity that is below the toxic level. Thus, for example, under the control of the calendar subsystem 11, a medication that is taken daily and toxic at 5 or more pills is delivered to the patient in quantities of 3 pills every three days. As discussed, the delivery costs per pharmacy letter are so low that such low-quantity delivery is cost-effective. Further, by including the deliveries as part of the usual daily mail deliveries, the postal pharmacy letters are not particularly inconvenient for the patient.

In addition, prescriptions for medication that may not be needed long term may be periodically filled in small quantities by the just in time delivery operations. The prescription may then be timely suspended by the prescribing doctor when the desired result occurs—e.g., infection alleviated, acute pain gone, and so forth. In this way, excess medication does not sit unused in the patient's medicine cabinet or get thrown away. Further, a doctor can check with the patient periodically to determine the need for the medication at all or if the dosages should be changed as a patients' condition gets better or worse, and write new prescriptions. The patient's medications can thus be adjusted, without requiring a patient to pay for full quantities of the various dosages.

Referring now also to FIGS. 4-8, we discuss the operations of the system 10 in more detail. When the system controller 12 receives a prescription, the controller consults the database subsystem 13 which includes a patient information database 131 that contains medication and medical condition information, and a medical interaction database 132 that contains drug interaction information and information relating to adverse medical conditions for the medications. The patient information database 131, which is entered using a patient's name or other identifying information, provides a listing of what other medications the patient may be taking and any medical conditions that may react adversely to medications (steps 400, 402). The system then consults the drug interaction database to determine if there is an indicated drug interaction between the newly prescribed medication and the previously prescribed medications or a medical condition that indicates a possible adverse reaction (step 404). If so, the system notifies a prescribing doctor to determine if the prescription should be filled (step 405). Otherwise, the controller assigns an identifier to the prescription and instructs the database subsystem to add an entry for the prescription into the patient information database (steps 406, 408). The controller then sends prescription-related information to the other system components, namely, the pill dispensing system 14, the packaging system 16 and the track and trace system 30 (step 410).

The system controller 12 sends to the pill dispensing system 14 information that identifies the medication and the number of pills required to fill the prescription. The pill dispensing system, operating in a known manner, directs a robotic subsystem 144 to dispense the prescribed pills from pill supply canisters 140. The robotic subsystem is thus directed to select and retrieve the supply canister of interest and count out the appropriate number of the pills. The robotic subsystem then provides the pills to a conveyancing subsystem 146, which transports the pills to the packaging system 16 (steps 500, 502, 504).

When the packaging system 16 receives prescription-related information, namely, the name and address of the patient, the name and registration number of the prescribing doctor, the medication prescribed, the pill count, and so forth, printer 162 prints certain of the medication and prescription information on the lid 24 of the associated carrier 20 and, as appropriate, the sleeve 26 of the carrier, an associated mailing label 28 and/or an associated carrier mailing envelope 27 (steps 600, 602). Further, as necessary, the printer prints boundary designations or lines 25 on or in the top surface 23 of the blister pack 21, to group the pills according to dosage.

If a printed sheet (not shown) that provides medication specific information relating to drug interactions, side effects, and so forth, is required, the system controller 12 instructs the packaging system controller 160 to print an associated file or instead sends the file to the packaging system printer 162.

Once the packaging system 16 receives the pills from the pill dispensing system 14, a feeder 164 feeds the pills into the compartments 22 of the blister pack 21 (step 604). If a single prescription is packaged per carrier 20, the feeder may sweep the pills into the compartments. If more than one prescription is to be packaged in a given carrier, the feeder may instead use a linear feeding mechanism and deposit the pills one by one into the appropriate compartments, as discussed in more detail with respect to FIG. 8 below.

The packaging system 16 may further include a camera 166 that records an image of the filled carrier 20. As shown, the carrier base may have printed thereon a code that includes the identifier that is assigned to the prescription by the system controller, and thus, the image and the prescription are readily matched. The image may thus be used by the system controller 12 to verify that the correct medication was included in a given pharmacy letter before the pharmacy letter is provided to the mail sorting machines 18.

Once the pills have been fed into the blister pack 21 and the contents verified, as appropriate, a sealing/folding station 168 seals the blister pack in a known manner, using, for example, a foil back sheet, and then folds the lid 24 over the blister pack and seals the lid in place by applying seals or an adhesive. The station 169 next inserts the blister pack into the sleeve 26, or alternatively slides the sleeve over the blister pack. As required, the station inserts printed information related to the medication into the sleeve. Alternatively, the station may wrap the insert around the blister pack before sliding the blister pack into the sleeve. The package may then be further sealed against tempering by joining the ends of the sleeve to produce a closed carton and/or by shrink wrapping or otherwise wrapping the carrier 20. In addition, the station may insert the carrier into a carrier envelope 27.

As discussed above, the packaging system 16 may print a mailing label 28 directly on the sleeve 26 or the system may print a separate mailing label that it then attaches, as appropriate, to the sleeve either before or after the assembly and wrapping of the carrier 20. The mailing label may instead be printed on or attached to the carrier envelope 27, either before or after the carrier is inserted in the envelope. As appropriate, postage is applied to the assembled carrier or carrier envelope 27. Preferably, the postage is printed on the mailing label or directly on the carrier mailing envelope.

The packaging system next provides the sealed and addressed carrier, i.e., the pharmacy letter, to the mail sorting machines 18 (step 608). As also discussed above, the mail sorting machines 18 sort the pharmacy letters in the same manner as the machines sort first class, or priority, mail pieces, that is, by postal routes based on the mailing addresses. The sorting machines thus provide the sorted pharmacy letters and the sorted first class, or priority mail pieces directly to the appropriate mail pouches 20 or to mail canisters 21 that transport the mail to local post offices for further sorting into the mail pouches 20, such that the pharmacy letters are hand-delivered along the postal routes as part of the daily postal first class, or priority, mail delivery operations.

Figure 7:
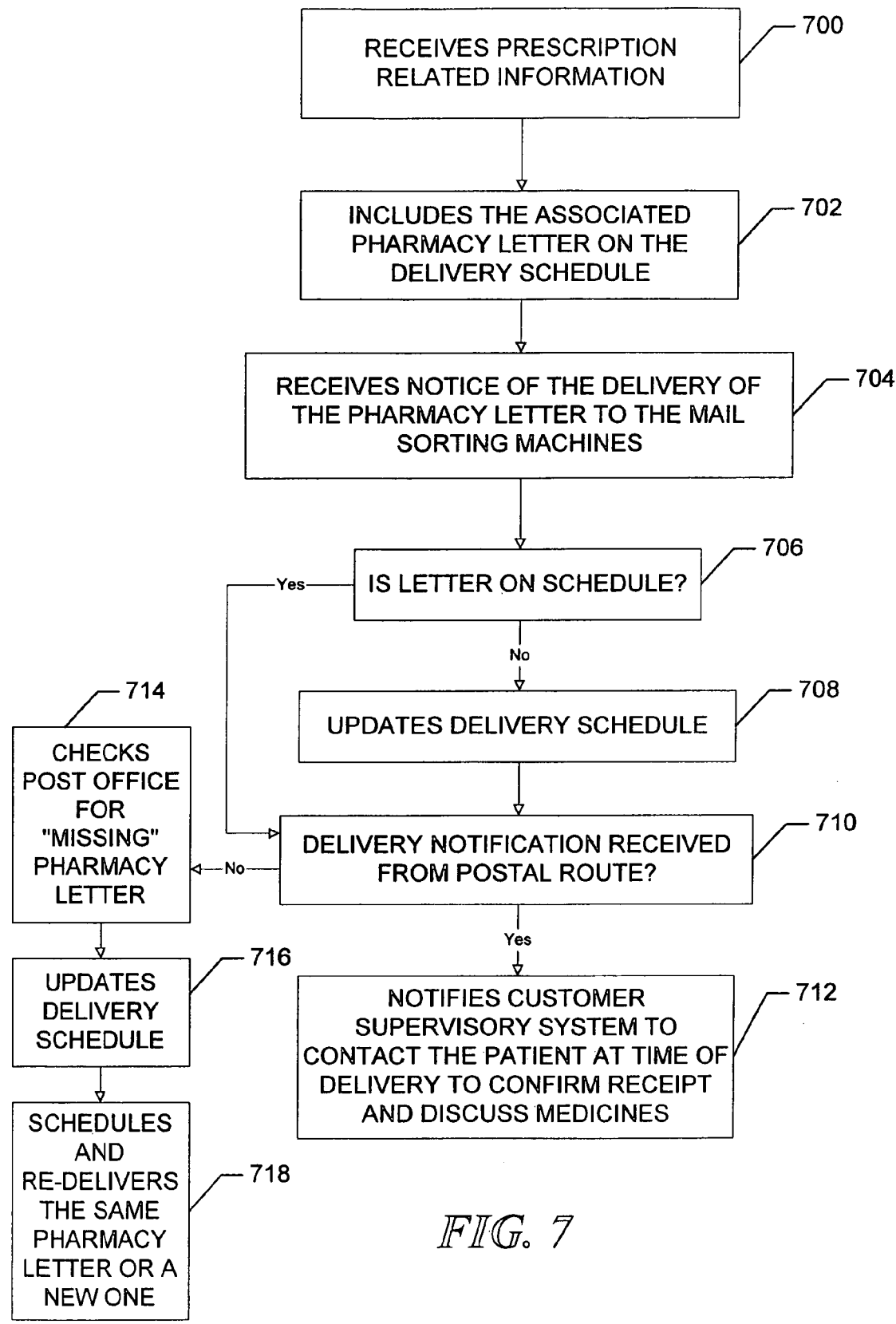

Referring also to FIG. 7, the track and trace system 30 receives prescription related information from the controller 12 and includes the associated pharmacy letter on a delivery schedule (steps 700, 702). When the track and trace system receives notice that a particular pharmacy letter has been assembled by the packaging system 16, the track and trace system determines if the pharmacy letter has met the mail sorting deadline imposed by the sorting machines 18 for same day delivery. The track and trace system then checks and, as appropriate, updates the delivery schedule accordingly (steps 704, 706, 708). The track and trace system makes the delivery schedule, or more precisely, relevant portions thereof, available on-line to the respective patients, prescribing doctors and postal pharmacy personnel.

When the track and trace controller 32 thereafter receives a delivery notification, i.e., the wireless communication by the wand 34 from the mail drop site, the controller updates the delivery schedule and sends a notice to the customer supervision system 36. The customer supervision system then contacts the patient, to both confirm receipt of the package by the patient and, as necessary, discuss the medications with the patient (steps 710, 712). As discussed in more detail below with reference to FIG. 9, the track and trace system controller also notifies the system controller 12, which provides the delivery information, as appropriate, to the calendar subsystem 11.

If the track and trace system 30 does not receive the delivery notification, the system waits for the evening return of the undelivered mail pieces, which may include undelivered pharmacy letters. Any undelivered pharmacy letters are scanned at the post office, to provide the associated identifiers to the track and trace system. Based on the identifiers, the track and trace system updates the delivery schedule to accommodate re-delivery of the undelivered pharmacy letters (steps 714, 716, 718). As appropriate, the track and trace system may inform the customer supervisory system 36, which then notifies the patient about the delayed delivery.

If a particular pharmacy letter is not found at the post office after the misdirected mail is returned for the day, the controller 12 re-directs the associated prescription-related information to the appropriate system components 14, 16 and 30, to again fill the prescription and provide another associated pharmacy letter for delivery through the postal system.

For re-filled prescriptions or prescriptions filled in small quantities over the prescription period, the system may use the personalized track and trace system described in U.S. Patent Publication 20020095306, which is owned by the assignee and incorporated herein by reference, to inform the patient about medication dosages, numbers of re-fills remaining, and so forth in messages that are associated with the on-line delivery information. The messages included in the track and trace information may be in lieu of or in addition to the telephone calls discussed above.

Figure 8:
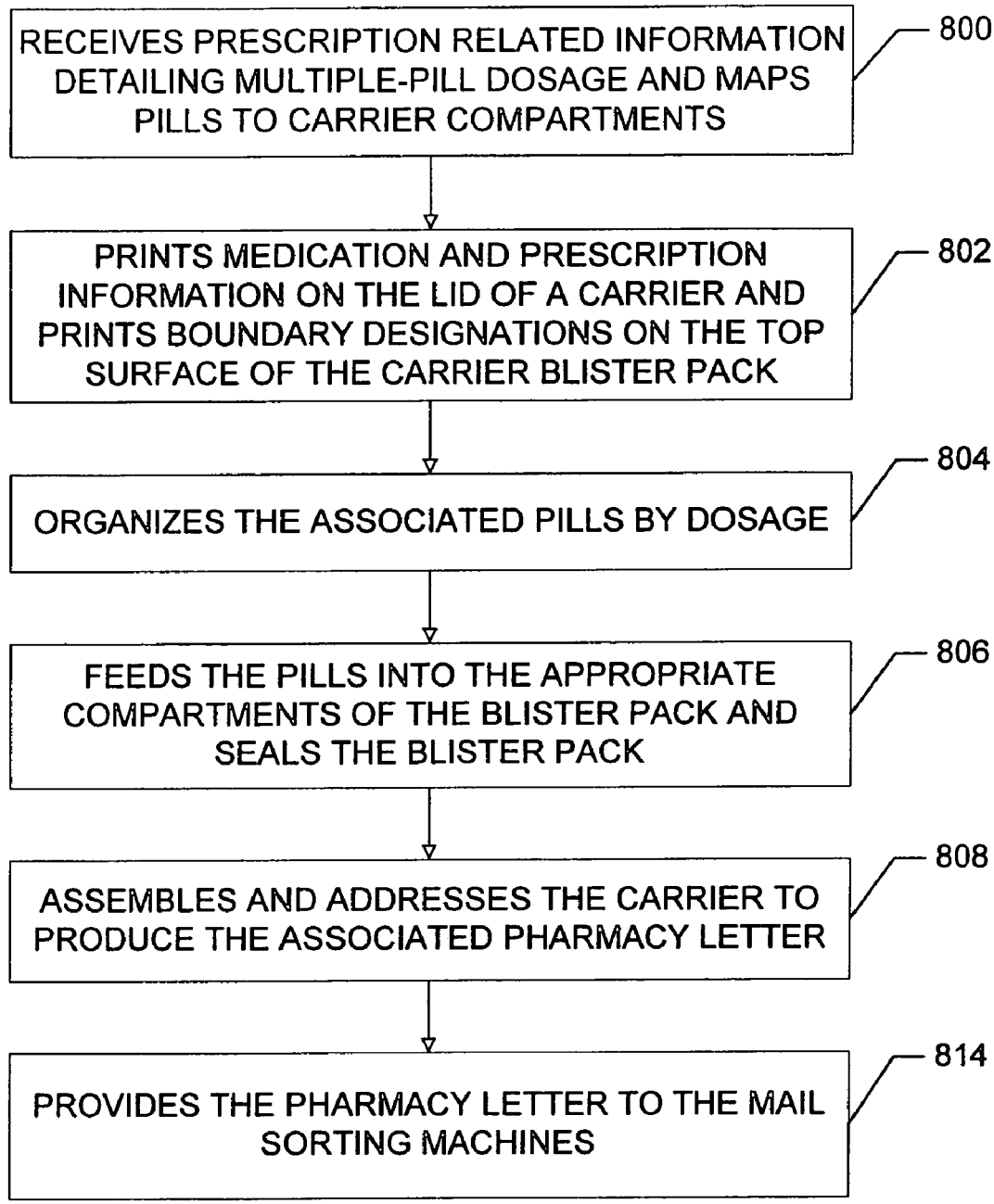

Referring now to FIG. 8, if the system combines multiple prescriptions in a single carrier 20, the packaging system 16 or the controller 12, as appropriate, essentially maps out which prescription pills go into the respective compartments 22 of the blister pack 21 (step 800). The packaging system then prints or embeds boundary designations on the top surface 23 of the blister pack, to denote the different medications, daily dosages, days of the week, and so forth. The packaging system also prints medication and/or prescription related information on the lid 24 of the carrier 20 and/or the sleeve 26 of the carrier (step 802).

The packaging system next fills the blister pack compartments 22 with the designated pills 200, 201 (steps 804, 806). The packaging system may first receive all of the pills designated for the various prescriptions, and organize and feed the pills in order into the compartments. Alternatively, the system controller 12 may direct the pill dispensing system to provide the pills for a first prescription and direct the packaging system to fill the compartments slated for that particular kind of pill. The controller then directs the pill dispenser to provide the pills for a next prescription and the packaging system to fill the compartments slated for these pills, and so forth.

Once the prescription medications are fed into the blister pack 21, the packaging system seals the blister pack and follows the steps set forth above to fully assemble, address and seal the carrier 20, i.e., to produce the associated pharmacy letter (step 808). The system then provides the pharmacy letter to the mail sorting machines 18, which include the pharmacy letters in the postal system first class, or priority, mail delivery operations (step 810).

Figure 9:
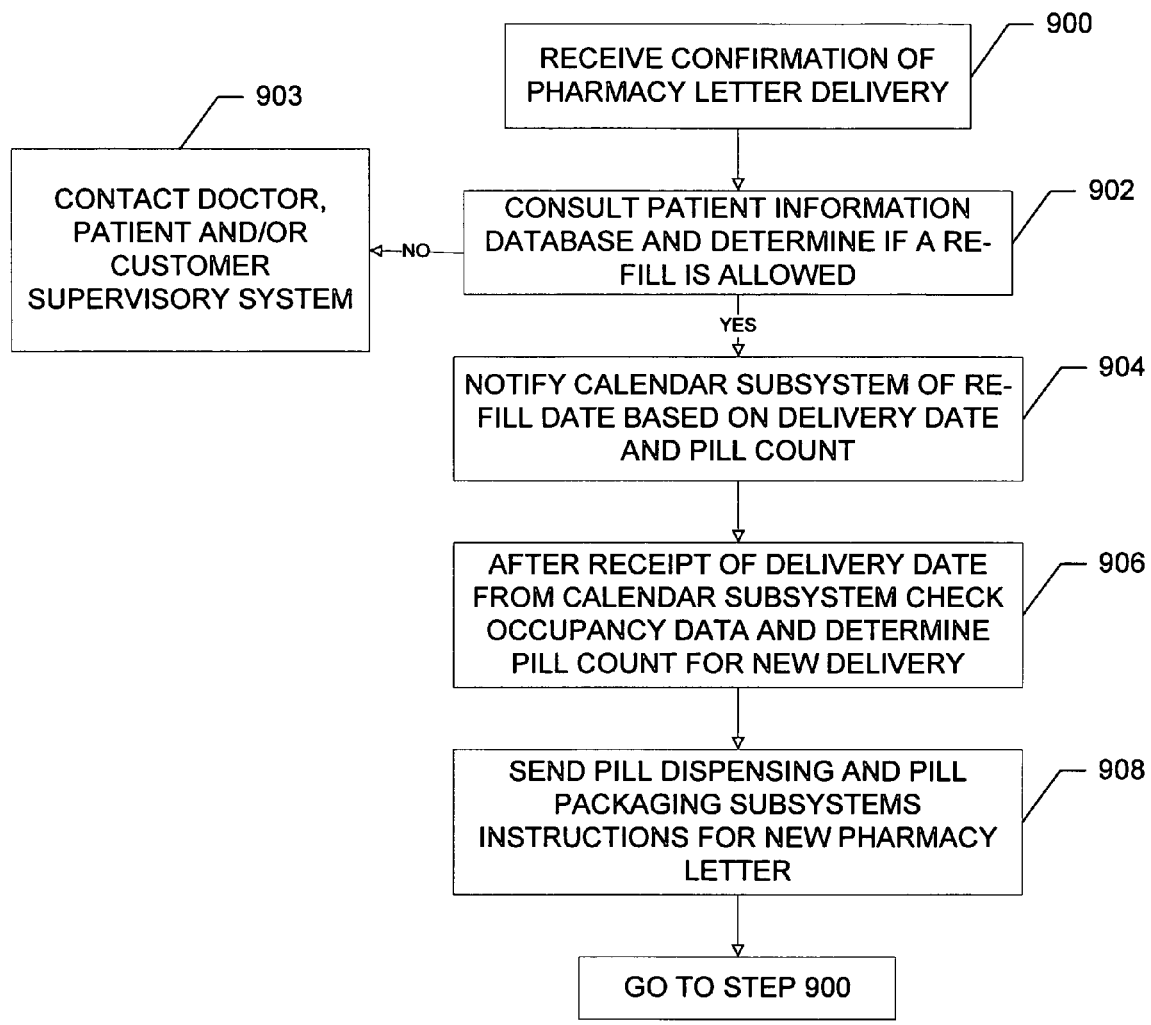
FIG. 9 is a flow chart of the just in time delivery operations.

Referring now also to FIG. 9, the system controller 12 controls the just-in-time delivery operations based on delivery confirmation information provided by the track and trace system 32 and the prescription information contained in the patient information database 131 (steps 900, 902). The system also keeps a record of the total number of pills or number of refills delivered to the patient to date for a given prescription and the date of at least the last pharmacy letter delivered.

When a delivery confirmation is received, the system controller determines if a re-fill or, as discussed above, another partial delivery, or installment, of a prescription is authorized (step 902). If not, the system controller notifies the doctor, the patient and/or the customer supervisory system 36 (step 903). If so, the controller then sets a refill date in its calendar subsystem 11 (step 904). On the appropriate date, the calendar subsystem notifies the controller, and the controller, in turn, sends instructions to the dispensing and packaging systems 14, 16.

Before determining how many pills to dispense, the system controller 12 may also check the occupant information to determine if children reside at the address, the medication information to determine the toxicity of the medication, and so forth to determine if installment delivery is appropriate (steps 906, 908). The system next prepares the pharmacy letter for the indicated number of pills and delivers the medication as part of the mail delivery operations. The system also calendars the next delivery date, based on the number of pills delivered, when delivery confirmation is received and, as appropriate, notifies the prescribing doctor.

The track and trace system may be expanded to track and trace the delivery of the pill containers, or canisters, 141 from the manufacturer to the postal pharmacy 10. As part of an expanded track and trace system 30, the pill canisters have printed on them or attached to them machine-readable codes that include tracking numbers in the form of, for example, bar codes or RFID tags. When the pill canisters leave the manufacturer's facility, the manufacturer provides to the track and trace system 30 the canister tracking codes and the specifics of the contents of the respective pill canisters, namely, information that identifies the amount and type of pills contained in a given canister and the date at which the canister left the facility.

When the pill canisters 141 are delivered to the pill dispensing system 16, the system reads the machine-readable codes and notifies the track and trace system 30 that the identified canisters have arrived. If a sealed canister has been tampered with, that is, the seal has been broken indicating that the canister has been opened, the pill dispensing system notifies both the track and trace system and the manufacturer of the condition of the canister. Otherwise, the pill dispensing system adds the canisters in the shipment to its inventory, and provides the manufacturer with delivery confirmation.

As pills are dispensed by the pill dispensing system, the system controller 12 may notify the manufacturer that a particular number of pills were dispensed from a given canister 141. The manufacturer then maintains a running count of the total number of pills dispensed from a given canister and provides to the pharmacy post office another canister shipment when the pharmacy post office inventory is depleted to a predetermined level.

The system described above may be used with some source-specific adaptations by doctors, veterinarians, hospitals, and other medical and pharmaceutic personnel to prescribe medications that will be hand-delivered through the postal service to the patients. In addition, the system may be used by non-medical personnel to order or "prescribe" non-prescription medications, such as holistic or alternative medications. The track and trace steps for the non-prescription medications may be relaxed, as appropriate, to omit the scanning of the non-prescription pharmacy letters at the mail drop points. Rather, the track and trace system may require that the postal delivery personnel scan the non-prescription pharmacy letters that are undeliverable, that is, those that are returned to the post office at the end of the daily postal delivery operations—with the system otherwise recording delivery of the non-prescription pharmacy letters at the end of the day. Further, with the non-prescription medication pharmacy letter deliveries, the customer supervisory system may instead contact the recipients the following day, or within a day or two, to confirm the delivery and discuss questions relating to use of the non-prescription medications.

For such duel use pharmacy letters, that is, use with prescription and non-prescription medications, the system includes on the mailing labels or on the carriers printing or some other indicia that instructs the postal delivery personnel if the respective pharmacy letters require scanning at the mail drop points.

Also, the system can be readily adapted to deliver other items commonly available through a pharmacy. For example, the system can package condoms or other small individual items in carriers, such as cartons, that meet the size requirements of the mail sorting machines and sort and deliver the items in the manner described above. Such items may be electronically ordered through, for example, websites that communicate with the controller 12. The track and trace requirements for these orders may also be relaxed, as discussed above, and/or the customer supervisory operations may be omitted. Again, the delivery which is same-day or next-day depending on the time at which the order for the item reaches the controller, adds only pennies to the price of the item.

The coupling of the pharmacy operations with the postal service delivery operations provides advantages beyond those associated with trusted, efficient and inexpensive delivery of the prescription medications. One such advantage is in medical crisis management. If, for example, an outbreak of an infectious disease, such as SARS or bird flu, occurs in a particular neighborhood, the postal service can readily identify addresses for the delivery of medication. The system may thus be coupled with a GIS system, to first identify the neighborhood of interest geographically and the number of registered occupants per dwelling. The postal service then provides the delivery address information, a hospital provides the prescription medication information, and the packaging system produces the associated pharmacy letters and provides them to the sorting machines, which sort the pharmacy letters into mail delivery pouches to direct the medication to the households in the affected area.

The foregoing description has been limited to a specific embodiment of this invention. It will be apparent, however, that variations and modifications may be made to the invention, with the attainment of some or all of its advantages. For example, the carrier may include a separable base or be one-piece, the carrier compartments may consist of raised walls or other physical separators instead of or in addition to the blister packaging compartments, the separate pill dispensing and packaging systems may be combined or separated into one or more other systems that together perform the automated dispensing and packaging, and so forth. Therefore, it is the object of the appended claims to cover all such variations and modifications as come within the true spirit and scope of the invention.

What is claimed is:

1. A system for packaging prescription medication as pharmacy letters, the system including:
   A. a system controller configured to receive a prescription and provide instructions for dispensing and packaging pills prescribed by the prescription;
   B. a pill dispensing system configured to receive instructions from the system controller and dispense pills from pill containers, the pill dispensing system including
      a robotic subsystem configured to select containers and count out pills in accordance with instructions received from the system controller, and
      a first conveyancing subsystem configured to convey the pills to a packaging system;
   C. a base with one or more compartments configured to receive the pills,
   D. a carrier configured to receive the base, the carrier conforming in size to a mail piece that is machine-sortable as a first class or priority letter;
   E. the packaging system, configured to receive the pills from the first conveyancing subsystem and instructions from the system controller, including
   a feeder configured to deposit the pills in the one or more compartments of the base,
   a printer configured to
      print prescription information on one or both of the base and the carrier, and
      print a mailing address of the patient on the carrier or on one or more labels for attaching to the carrier, and
   an assembly station configured to assemble and seal the carrier and the base to enclose the pills and conceal the prescription information and display the mailing address to produce the pharmacy letter as a machine-sortable first class or machine-sortable priority letter, wherein a carrier and base sealed by the assembly station together have a thickness of 7 millimeters or less;
   a second conveyancing subsystem coupled to the assembly station and an automated mail sorter machine configured to convey the pharmacy letter from the assembly station to an automated mail sorter machine; and
   E. the automated mail sorter machine, configured to receive the pharmacy letter from the second conveyancing subsystem and sort the pharmacy letters along with other types of machine sortable first class or priority mailpieces for delivery over different postal delivery routes in accordance with the mailing addresses.

2. The system of claim 1 wherein the mailing address information is printed also as a bar code and the automated mail sorter scans the bar code to obtain the mailing address information.

3. The system of claim 1 wherein
   the packaging subsystem includes a camera that takes one or more pictures of the base after the pills for a given prescription are deposited in the base, the camera providing the pictures to the controller, and
   the controller determining from the pictures and the associated prescription information if the correct medication is contained in the base before instructing the packaging subsystem to assemble the pharmacy letter.

4. The system of claim 1 wherein the controller further
   determines how many of the pills from a given prescription to deliver at a given time and instructs the pill dispensing system and the pill packaging system, and
   keeps track of the number of pills delivered and the date and instructs the pill dispensing and pill packaging systems to produce another pharmacy letter for the delivery of additional pills from the given prescription to provide the pills in time to replenish the patient's supply.

5. The system of claim 1 further including
   the system controller assigning tracking identifiers to the respective prescriptions;
   the packaging system including on the pharmacy letters machine readable codes that include the tracking identifiers;
   a track and trace system for determining and updating delivery schedules for the respective pharmacy letters, the track and trace system including
   a controller for maintaining delivery schedules based on when the respective pharmacy letters are provided to the mail sorting machines,
   a wireless scanner/transmitter for scanning or reading identifier information from the pharmacy letters and transmitting delivery confirmations when the pharmacy letters are deposited at patient drop-off sites,
   the controller receiving the delivery confirmations and updating the delivery schedules.

6. The system of claim 5 further including a customer satisfaction system for receiving the delivery confirmations from the track and trace system and contacting the patient to provide associated prescription related information.

7. The system of claim 1 further including
   a government information system database which contains geographic and residential occupancy information,
   the system controller, in response to pill designations and geographic area and residency information from the database, providing instructions for the preparation of pharmacy letters to deliver the designated pills to the residents in the specified geographic area.

8. The system of claim 1 further including
   a database system for receiving prescription information from the system controller and providing to the system controller indications of adverse patient reactions, the database system including a patient information database that contains medication and medical condition information and a drug interaction database;

the system controller responding to the indications by contacting the prescribing doctor for permission before instructing the system to fill the prescription.

9. A pharmacy-post office including:
A. one or more automated mail sorting machines configured to sort mail pieces by postal delivery routes and provide the sorted mail pieces for postal delivery;
B. a system controller configured to receive prescriptions and provide prescription information and instructions for dispensing and packaging the prescriptions to other system components;
C. a pill dispensing system configured to select pill containers and count out pills in accordance with instructions received from the controller;
D. a base with one or more compartments configured to receive the pills;
E. a carrier configured to receive the base, the carrier and base together conforming in size to a mail piece that is machine-sortable by the mail sorting machines; and
F. a packaging system configured to
  receive the base and carrier, the medication for one or more prescriptions from the pill dispensing system and packaging instructions from the system controller and selectively deposit the pills in the compartments of the base in accordance with the instructions,
  receive prescription information and a mailing address from the system controller and print the prescription information on one of the base and the carrier and the mailing address on the carrier or one or more labels for attaching to the carrier,
  assemble the base and the carrier as a pharmacy letter to enclose the pills and the prescription information and display the mailing address information, wherein a carrier and base assembled by the packaging system together have a thickness of 7 millimeters or less;
G. a conveyancing sub-system coupled to the packaging system and the automated mail sorting machines configured to convey the assembled pharmacy letter to the automated mail sorting machines and feed the pharmacy letter into the mail sorting machines; and
H. the automated mail sorting machines configured to sort the pharmacy letters along with other types of machine sortable mailpieces from other sources for inclusion of the pharmacy letters and the other types of machine sortable mailpieces in different postal delivery routes based on the mailing addresses.

10. The pharmacy post office of claim 9 wherein the controller
determines how many of the pills from a given prescription to deliver at a given time and instructs the pill dispensing system and the pill packaging system,
keeps track of the number of pills delivered and the date and instructs the pill dispensing system and pill packaging system to dispense additional pills from the given prescription at a date that replenishes the patient's supply.

11. The pharmacy post office of claim 10 further including
the system controller assigning a tracking identifier to the prescription;
the packaging system including on the pharmacy letter a machine readable code that includes the identifier; and
a track and trace subsystem for determining and updating one or more delivery schedules for the respective pharmacy letters, the track and trace system including:

a controller for maintaining the one or more delivery schedules based on when the respective pharmacy letters are provided to the mail sorting machines,
a wireless scanner/transmitter for reading the codes and transmitting delivery confirmations when pharmacy letters are scanned before deposit at associated drop-off sites,
the controller receiving the delivery confirmations and updating the one or more delivery schedules.

12. The pharmacy post office system of claim 9 further including
a government information system database which contains residential occupancy information,
the system controller providing instructions in response to pill designations and geographic area information from the database for the preparation and delivery of pharmacy letters to provide the designated pills to the residents in the specified geographic area.

13. A method for packaging prescription medication as a pharmacy letter, the method including the steps of:
A. receiving a prescription and determining how many pills to deliver to the patient;
B. instructing a robotic subsystem to
  dispense the pills;
  receive a base with one or more compartments that receive the pills and a carrier for receiving the base and conforming in size to a mail piece that is machine-sortable by mail sorting machines;
  feed the pills to the one or more compartments in the base;
  print prescription information on one of the carrier and the base and a mailing address on the carrier or one or more labels for attaching to the carrier;
  assemble the carrier and the base at an assembly station to enclose the pills and the prescription information and display the mailing address information for reading by machine to produce the pharmacy letter as a machine-sortable mail piece, wherein the assembled carrier and base have a thickness of 7 millimeters or less; and
  convey the pharmacy letter to and feeding the pharmacy letter into an automated mail sorter machine that sorts the pharmacy letter along with other types of machine sortable mail pieces into different postal delivery routes in accordance with the mailing addresses, the conveying performed over a conveyancing subsystem that is coupled to the assembly station and the automated mail sorter.

14. The method of claim 13 further including the steps of
taking an image of the base after the pills for a given prescription are deposited in the base, and
verifying the correct pills are included in the base before the base and carrier are assembled.

15. The method of claim 13 further including the steps of
keeping track of the number of pills delivered and the date of delivery, and
repeating step B to package additional pills from the given prescription in a next pharmacy letter for delivery to the patient.

16. The method of claim 13 further including the steps of
associating tracking identifiers with the respective prescription,
including the tracking identifiers on the corresponding pharmacy letters,
maintaining delivery schedules based on the time and date the respective pharmacy letters are provided to the mail sorting machines, scanning or reading identifier information from the pharmacy letters and transmitting delivery confirmations when the pharmacy letters are deposited at associated drop-off sites, and updating the one or more delivery schedules when delivery confirmations are received.

17. The method of claim 13 further including the steps of receiving residential occupancy information, prescription medication information, and geographical area information, and repeating step B to prepare pharmacy letters to deliver designated medications to the residents in the specified geographic area.

18. A method for delivery of prescription medication through post office delivery routes, the method including the steps of:
   A. receiving prescriptions;
   B. instructing a robotic pill dispensing subsystem to select and count out pills;
   C. receiving a base with one or more compartments that receive the pills and a carrier for receiving the base, the carrier and base together conforming in size to a mail piece that is machine-sortable by automated mail sorting machines;
   D. feeding the pills into the one or more compartments of the base and including on or in one or both of the base and the carrier prescription related information;
   E. printing on or applying to the carrier a mailing address;
   F. at an assembly station, assembling the base and carrier to enclose the pills and the prescription related information and display mailing address information so as to be readable by the automated mail sorting machines to produce a pharmacy letter, wherein the assembled carrier and base have a thickness of 7 millimeters or less;
   G. conveying the pharmacy letter to and feeding the pharmacy letter into an automated mail sorting machine that sorts the pharmacy letters along with other types of machine sortable mail pieces from other sources for delivery on different postal delivery routes based on the mailing address information, the conveying being over a conveyancing subsystem that is coupled to the assembly station and the automated mail sorter; and
   H. delivering the pharmacy letters along with the other types of mail pieces over the postal delivery routes to the patients.

19. The method of claim 18 further including the steps of associating tracking identifiers with the respective prescriptions, providing the tracking identifiers on the corresponding pharmacy letter, maintaining one or more delivery schedules for the respective pharmacy letters based on when the pharmacy letters are provided to the mail sorting machines, reading the identifiers and transmitting delivery confirmations when pharmacy letters are deposited at associated drop-off sites, and updating the one or more delivery schedule database.

20. The system of claim 9 wherein the packaging system further applies postage to the carrier.

21. The method of claim 18 further including applying postage to the pharmacy letter.

* * * * *